(12) United States Patent
Nichols

(10) Patent No.: US 6,407,040 B1
(45) Date of Patent: Jun. 18, 2002

(54) COMPOSITION AND METHOD FOR REDUCING TRANSPIRATION IN PLANTS

(75) Inventor: Everett J. Nichols, Edmonds, WA (US)

(73) Assignee: Vanson, Inc., Redmond, WA (US)

( * ) Notice: Subject to any disclaimer, the term of this patent is extended or adjusted under 35 U.S.C. 154(b) by 0 days.

(21) Appl. No.: 09/641,451

(22) Filed: Aug. 17, 2000

Related U.S. Application Data

(63) Continuation-in-part of application No. PCT/US99/03628, filed on Feb. 19, 1999.
(60) Provisional application No. 60/149,939, filed on Aug. 19, 1999, and provisional application No. 60/075,455, filed on Feb. 20, 1998.

(51) Int. Cl.$^7$ ................................................ A01N 43/08
(52) U.S. Cl. ........................................ 504/140; 504/299
(58) Field of Search ................................... 504/140, 299

(56) References Cited

U.S. PATENT DOCUMENTS

| 4,199,496 | A |   | 4/1980 | Peniston et al. ........ 260/112 R |
| 4,812,159 | A |   | 3/1989 | Freepons ........................ 71/16 |
| 4,964,894 | A |   | 10/1990 | Freepons ........................ 71/88 |
| 5,374,627 | A | * | 12/1994 | Ito et al. ........................ 514/55 |
| 5,496,933 | A |   | 3/1996 | Kelkenberg .................. 536/20 |
| 5,726,123 | A |   | 3/1998 | Heinsohn et al. ............ 504/140 |
| 5,733,851 | A | * | 3/1998 | Villanueva et al. ......... 504/292 |
| 6,167,652 | B1 | * | 1/2001 | Heinsohn et al. ............. 47/58.1 |

FOREIGN PATENT DOCUMENTS

| EP | 0 592 964 A1 | 4/1994 |
| WO | WO 98/32335 | 7/1998 |

OTHER PUBLICATIONS

Abstract of JP 53–059027, May 1978.*

* cited by examiner

*Primary Examiner*—S. Mark Clardy
(74) *Attorney, Agent, or Firm*—Christensen O'Connor Johnson Kindness PLLC

(57) ABSTRACT

A composition and method for reducing plant transpiration and preventing drought-induced wilting and for reducing water use by crops is disclosed. The composition includes an aqueous solution of chitosan and a nonphytotoxic acid. In an embodiment, the chitosan is derived from ground fungal mycelia.

18 Claims, 14 Drawing Sheets

COMPOSITION AND METHOD FOR REDUCING TRANSPIRATION IN PLANTS

CROSS-REFERENCE TO RELATED APPLICATIONS

This application is a continuation of copending U.S. provisional patent application No. 60/149,939, filed Aug. 19, 1999, and a continuation-in-part of copending international patent application No. PCT/US99/03628, filed Feb. 19, 1999, which is a continuation of U.S. provisional patent application No. 60/075,455, filed Feb. 20, 1998, the benefit of the priority of the filing dates of which is hereby claimed under 35 U.S.C. §§ 119 and 120. Each of the above-identified applications is expressly incorporated herein by reference in its entirety.

FIELD OF THE INVENTION

The present invention relates to a composition and method for reducing plant transpiration and, in particular, to a chitosan composition and method for applying the chitosan composition to plant foliage to reduce transpiration, to reduce drought-induced wilting, and to reduce water use by crops.

BACKGROUND OF THE INVENTION

Drought poses a serious problem for agriculture. Water shortages can greatly adversely affect crop yield. While crop irrigation during periods of low rainfall and drought is a solution to decreased crop yield and plant death, significant expense is associated with irrigation. Thus, alternatives to irrigation including methods for maintaining healthy crops during drought periods are continuously sought.

The present invention relates to a chitosan composition and method for reducing transpiration and preventing drought-induced wilting in plants. In the method, a chitosan composition is applied to plant foliage in an amount and with a frequency sufficient to affect a reduction in transpiration and wilting.

Chitosan is a derivative of chitin, a polysaccharide consisting predominantly of unbranched chains of N-acetyl-D-glucosamine residues (i.e., β-1,4-linked 2-acetamido-2-deoxy-D-glucose). Chitosan is produced by the deacetylation of chitin. Chitin can be regarded as a cellulose derivative in which the C-2 hydroxyl groups have been replaced by acetamido residues. Chitin is found in fungi, yeast, and abundantly in marine invertebrates and arthropods where it is a principal component of the exoskeleton. Chitin is commercially available from a number of sources and is typically prepared from crab shells. Chitin and chitosan are polysaccharides that differ in the extent of glucosamine acetylation. Pure 100% acetylated chitin does not occur naturally and chitosan is generally not 100% deacetylated. Rather, chitin polysaccharides consist of both acetylated and non-acetylated glucosamine residues within the polysaccharide chains. The percentage of acetylated D-glucosamine residues within chitin polysaccharide chains is higher compared to the non-acetylated D-glucosamine residues. Similarly, chitosan polysaccharides consist of both acetylated and non-acetylated D-glucosamine residues but contain a higher percentage of non-acetylated D-glucosamine residues relative to acetylated D-glucosamine residues.

Chitin has been used for a wide variety of purposes. For example, chitin has been used in wound healing compositions, as an adhesive, as a sizing agent for paper, and as a separation agent. The use of chitin as a plant fertilizer is described in U.S. Pat. No. 4,199,496, issued to Peniston et al. As a fertilizer, chitin is added to soil to supply chemical elements (e.g., nitrogen) needed for plant nutrition. Chitin slowly releases nitrogen into the soil thereby increasing the nitrogen content of the soil over a relatively long period of time.

Chitosan has been used as a plant growth regulator, a compound that can inhibit, accelerate, or otherwise influence physiological processes in plants. As described in U.S. Pats. Nos. 4,812,159 and 4,964,894, issued to Freepons, plant growth regulators are substances that are used to influence the growth characteristics of plants and cause some change in the plant's normal growth pattern. Plant growth regulators influence, for example, germination enhancement, root stimulation, plant stature control, shortening or lengthening of the time to plant maturity, ripening control, increased yield, color control, and shortened or lengthened dormancy.

The Freepons patents describe processes for influencing plant growth by distributing an aqueous solution of deacetylated chitin (i.e., chitosan) in a nonphytotoxic acid (preferably an amino acid) in the soil in which plants are to be grown. These patents note that the chitosan solution can also be applied directly to plant seeds or to the foliage of emerging plants.

Despite the advances in methods for improving agricultural methods, there exists a need for methods and compositions that reduce transpiration and prevent drought-induced wilting of plants. The present invention seeks to fulfill these needs and provides further related advantages.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
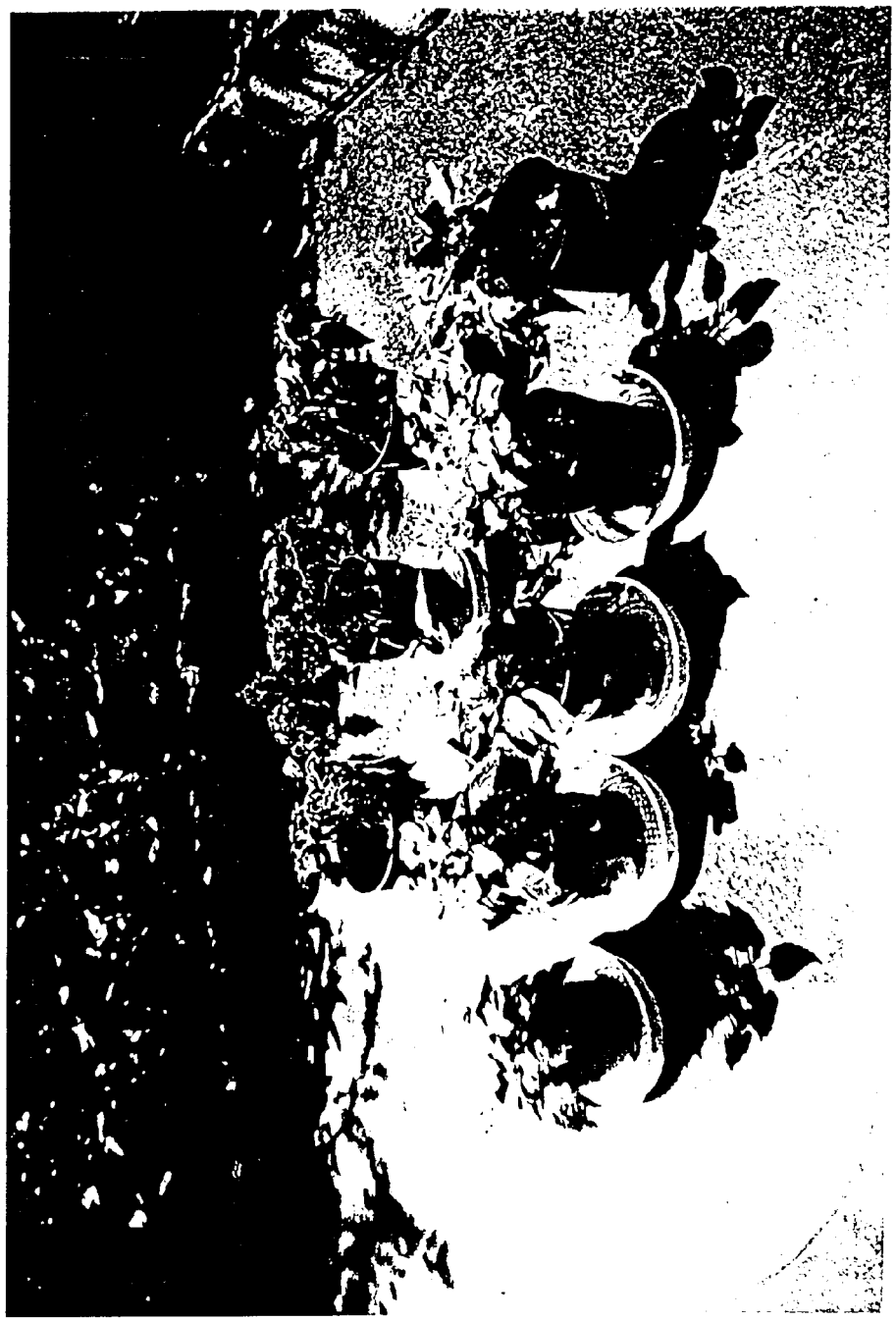
FIG. 1 is a photograph that compares pepper plants that have been subjected to drought conditions; pepper plants treated with chitosan according to the method of the present invention appear in the foreground, and untreated pepper plants appear in the background.

The present invention provides a composition and method for reducing transpiration in plants. The composition of the present invention is an aqueous solution of chitosan and a nonphytotoxic acid. The method of this invention includes the foliar application of the chitosan composition to effect reduced transpiration and prevent drought-induced wilting in plants. Plants treated with dilute chitosan solutions prior to the imposition of drought conditions remain turgid, healthy and green compared to untreated plants, which wilt when subjected to drought.

Chitosan is a key ingredient in the composition of the present invention. Chitosan is a deacetylated form of chitin and is commonly referred to as poly(D-glucosamine). Chitosan can be obtained by reacting chitin with concentrated aqueous potassium hydroxide at temperatures above about 40° C. The process effects chitin deacetylation. While the extent of deacetylation does not appear to be critical to the effectiveness of the composition and method of the present invention, chitosan that is approximately 76% deacetylated is particularly effective.

Chitosan is commercially available from a number of sources in several forms that vary with respect to the extent of deacetylation and molecular weight. For example, low, medium, and high molecular weight chitosan having viscosities of 20–200 cps, 200–800 cps, and 800–1000 cps, respectively, are available from Aldrich Chemical Company (Milwaukee, Wisconsin). These viscosities are reported in units of Centipoise (cps) for 1% chitosan solutions in 1% acetic acid. Practical grades of chitosan having viscosities greater than 200 cps prepared from crab shells are also commercially available. In one embodiment, an approximately 22 cps chitosan solution is preferred. A preferred commercial source of chitosan is Vanson Inc., Redmond, Wash.

Commercially available chitosan is typically prepared from shellfish and has a molecular weight measured in the hundreds of thousands, which corresponds to polymer chains containing several thousand linked monomer units. The range of molecular weights obtained from chitosan preparations can vary depending on the particular preparation method. In the practice of the present invention, suitable chitosan can be obtained from chitosan preparations having molecular weight distributions in the range from about 10,000 to about 500,000 Daltons, preferably from about 10,000 to about 50,000 Daltons. These molecular weights correspond to chitosan polymers having degrees of polymerization (DP) from about 60 to about 3,000, for 10,000 and 500,000 Dalton molecular weights, respectively, and from about 60 to about 300, for 10,000 and 50,000 Dalton molecular weights, respectively. The DP values are based on the chitosan being about 76% deacetylated. In a preferred embodiment, the chitosan has a molecular weight of about 20,000 Daltons.

In a preferred embodiment, the chitosan is derived from shrimp and is characterized as being about 76% deacetylated and having a 1% Brookfield Viscosity of about 22 cps. Based on the Brookfield Viscosity, the chitosan has a peak molecular weight of about 22,000 Daltons, which corresponds to a degree of polymerization of about 130.

In another preferred embodiment, the chitosan is derived from ground fungal mycelia, which contain chitin and/or chitosan in their cell walls. Preferred fungal groups from which chitosan can be obtained include Zygomycetes, specifically the Mucorales (Mucor, Rhizopus, Phycomyces) and Entomophthorales (Basidiobolus and Entomophthora). *Mucor rouxii* is a commonly studied fungal mycelia and contains up to about 33 percent by weight (based on total dry weight) chitosan in its cell walls. Ground fungal mycelia can be mixed with dilute acid to form a suspension that includes soluble and insoluble chitosan. The suspension can be used as formed and applied foliarly and as described below. Alternatively, the insoluble materials can be separated from the suspension by filtration or centrifugation, and the solution applied as described below.

The chitosan composition of the present invention is an aqueous solution of chitosan and a nonphytotoxic acid. Although the concentration of chitosan in the solution applied to plants is not particularly critical, the effective concentration will depend on the nature of the chitosan, particularly the molecular weight of the chitosan polymer and the viscosity of the polymer solutions. For example, compositions having greater than about 1% by weight chitosan can be effective and readily applied by spraying when the viscosity of the solution is relatively low due to relatively low molecular weight chitosan polymers. Generally, the composition of the invention includes chitosan in an amount from about 0.05 to about 10% by weight, preferably from about 0.05 to about 1.0% by weight, and more preferably about 0.1% by weight based on the total weight of the solution. An effective 0.1% chitosan solution can be prepared, for example, by tenfold dilution with water of a stock 1% chitosan solution in a 1% aqueous acid solution.

In addition to chitosan, the composition of the present invention includes a nonphytotoxic acid. As used herein, the term "nonphytotoxic acid" refers to an acid that, when used in the amounts prescribed, does not have a significantly adverse effect on the plant to which the solution is applied. Suitable nonphytotoxic acids include organic acids such as acetic, lactic, pyruvic, succinic, fumaric, glutamic, aspartic, malic, maleic, sorbic, salicylic, linolenic, jasmonic, β-D-glucopyranuronic, β-D-galactopyranuronic, β-D-mannopyranuronic, β-D-idopyranuronic, galacturonic, and iduronic acids. Preferred organic acids, including amino acids, are those that participate in the Krebs cycle and are involved in energy (ATP) production. Lactic acid is a preferred nonphytotoxic acid.

The nonphytotoxic acid is present in the composition in an amount from about 0.05 to about 10% by weight, preferably from about 0.05 to about 1.0% by weight, and more preferably about 0.1% by weight based on the total weight of the composition.

Other compositions that include chitosan in combination with other known substances that exhibit antitranspirant activity can also be useful in the method of the present invention. Examples of substances having antitranspirant activity include sorbitol, mannitol, and sucrose. The combination of chitosan with such antitranspirant agents may provide particularly useful compositions and methods that further reduce transpiration. Chitosan compositions may impart other desirable effects to plants including, for example, disease resistance.

Figure 2:
FIG. 2 is a closeup view of the plants of FIG. 1.

In another aspect, the present invention provides a method for reducing transpiration and drought-induced wilting in plants. In the method, a chitosan solution is applied to either the plant leaf surfaces or the plant base for delivery to the plant's root system prior to the onset of drought conditions. For plant leaf application, the solution application is preferably sufficient to wet the plant leaves by, for example, spraying a chitosan solution onto leaf surfaces. For plant root system delivery, a chitosan solution can be delivered by, for example, drip irrigation. The amount and frequency of the application of the chitosan solution to the plant to effect a reduction in transpiration and prevention of wilting varies depending upon the plant's environment. In one embodiment, the method includes applying a 0.1% chitosan solution to a plant once per week for three weeks prior to drought onset. Following such a procedure, treated plants did not wilt compared to control plants when drought conditions were imposed. In contrast to wilted, untreated plants, the chitosan-treated plants maintained turgor, and appeared healthy and green compared to the untreated control plants. The effectiveness of the method and composition of the present invention in preventing drought-induced wilting is shown in FIGS. 1 and 2. Chitosan-treated and untreated pepper plants that were subjected to drought conditions are shown in FIGS. 1 and 2. In FIGS. 1 and 2, the chitosan-treated pepper plants (foreground) appear healthy while the untreated plants (background) appear wilted. Treated plants were sprayed on leaf surfaces with a solution of chitosan dissolved in DL-lactic acid or β-D-galactopyranuronic acid. Concentration of chitosan was 0.1% (w/w) in water containing DL-lactic acid or β-D-galactopyranuronic at a concentration of 0.1% (w/w). Control treated plants were sprayed on leaf surfaces with water containing β-D-galactopyranuronic acid at 0.1% (w/w) or water containing DL-lactic acid at 0.1% (w/w).

Without being limited to the following theory, it is believed that the application of the chitosan solution to a plant's foliage according to the method of this invention reduces transpiration by the closing the plant's stoma. Stoma are the minute openings in the epidermis of plants that are regulated by guard cells and through which gases and water vapor are exchanged from the plant's internal spaces and the external atmosphere. Thus, stoma closure induced by the application of the chitosan solution according to the method of the present invention may be responsible, at least in part, for the reduction in transpiration, the prevention of drought-induced wilting, and the reduction of water use in plants. Reducing transpiration may impact plant physiology in a positive way such as increasing fruit production and/or biomass production. Transpiration reduction may influence the expression of certain genes involved in stress-related functions including disease resistance responses. Chitosan treatment according to the present invention may therefore be useful in treating plants prior to transplant to prevent transplant shock and death.

Foliar application of the chitosan compositions of the present invention results in a reduction of stomatal conductivity, which is indicative of stomatal closure. Reduction of stomatal conductivity results in decreased transpiration and lower water use for chitosan-treated plants. Thus, in addition to drought protection, foliar application of the chitosan compositions of the invention affords improved plant water status for treated plants.

Accordingly, in another aspect of the present invention, a method for reducing water use in plants and crops is provided. In the method, a chitosan solution is applied to either the plant leaf surfaces or the plant base for delivery to the plant's root system during the plant's growing period. For plant leaf application, the solution application is preferably sufficient to wet the plant leaves by, for example, spraying a chitosan solution onto leaf surfaces. For plant root system delivery, a chitosan solution can be delivered by, for example, drip irrigation. The amount and frequency of the application of the chitosan solution to the plant to effect a reduction in transpiration and corresponding reduction in water use varies depending upon the plant's environment.

The application of the chitosan compositions of the invention to crops has been found to significantly reduce the amount of water used by crops (e.g., corn, pepper, sunflower, and potato) and, in some instances, to increase biomass production. Chitosan treatment also increases the water use efficiency of the plant by inducing a different partitioning (i.e., a higher proportion of leaf tissue relative to stem tissue) compared to nonchitosan-treated plants.

As described in the following examples, foliar application of the chitosan compositions of the invention can reduce water used for irrigation by as much as about 60%. Such a reduction of irrigation water represents a significant economic savings. The demand for water continues to grow, with over 80% of water consumption being used for irrigation of crops.

In the following examples, the compositions' optimal chitosan concentration was determined under growth chamber conditions. The most effective concentration was determined to be about 0.1% chitosan (w/w) in 0.1% D/L-lactic acid (w/w). A composition having a 0.01% chitosan concentration did not show statistically significant differences using the same chitosan source at 0.1%. The optimal foliar application schedule was determined to be once per week. No significant reduction in water use was apparent at a frequency of one application every two weeks.

The composition and methods of the present invention generally relate reducing transpiration in plants by treating the plants with a chitosan composition. A wide variety of plants can be advantageously treated by the methods of the present invention. Among the plants that may be treated by the methods are edible plants including vegetable plants.

EXAMPLES

Example 1

Stomata Conductance and Transpiration in Greenhouse-Grown Plants

Dwarf sunflower (*Helianthus annuus* L.) plants were grown from seed in 20-cm diameter plastic pots. Each pot contained one plant growing in a peat, sand mixture. The plants were grown in a greenhouse with a 15 h light period and a radiation flux of 450 to 550 $\mu$mol/m$^2$ provided by lamps. Daytime and nighttime temperatures were 26° C. and 16° C. respectively. Relative humidity ranged between 30% to 40%. Plants were watered to field capacity daily. The chitosan treatment group and the control group consisted of 7 plants in each group.

The chitosan used in these experiments exhibited the following characteristics: deacetylation—76%; viscosity—22 cps (1% in 1% acetic acid); species—shrimp. Approximately 60 ml of chitosan (0.1% (w/w) solubilized in distilled water containing 0.1% D/L-lactic acid) was sprayed onto the top surface and bottom surface of leaves of 7 plants in the treatment group using a simple hand sprayer. The control group received approximately 60 ml of distilled water alone, sprayed onto the leaves in the same fashion as the treated group. Both the treated group and the control group were sprayed once a week on March 24, March 31, April 14, April 21, April 28, May 5.

Stomata conductance was measured with a steady state porometer (LiCor model LI-1600, LiCor Inc., Lincoln, Nebr.). Measurements were made on the abaxial leaf surfaces where the majority of stomata are located and were recorded on the following dates: March 31, April 2, April 7, April 9, April 16, April 29, May 5, and May 12.

The transpiration rate was determined by calculating the vapor pressure at the evaporating surface (leaf) and the air vapor pressure. The saturated vapor pressure of the leaf was calculated by measuring leaf temperature. Leaf temperature was measured using an external thermocouple as well as the LICor porometer. The air vapor pressure was determined from the relative humidity and air temperature according to the following equation: $e_a = e_s * hr$ where $e_s$ is the saturated vapor pressure at the air temperature, $e_a$ is the actual vapor pressure and hr is the relative humidity. The saturated vapor pressure can be obtained from tables or diagrams which relate vapor pressure to temperature and relative humidity. Relative humidity was determined using a sling psychrometer. Transpiration rates were determined from the stomata conductance and vapor pressures according to the following equation:

$$E = g_v (e_s - e_a / pa)$$

where E= transpiration rate, $e_s$ is the vapor pressure at the saturated surface (leaf), $e_a$ is the air vapor pressure and pa is the atmospheric pressure. Stomata conductance and transpiration were calculated for a single leaf without extrapolating to the entire plant. Averages for 7 plants of each group were calculated and plotted. The result is shown in FIG. 3.

Figure 3:
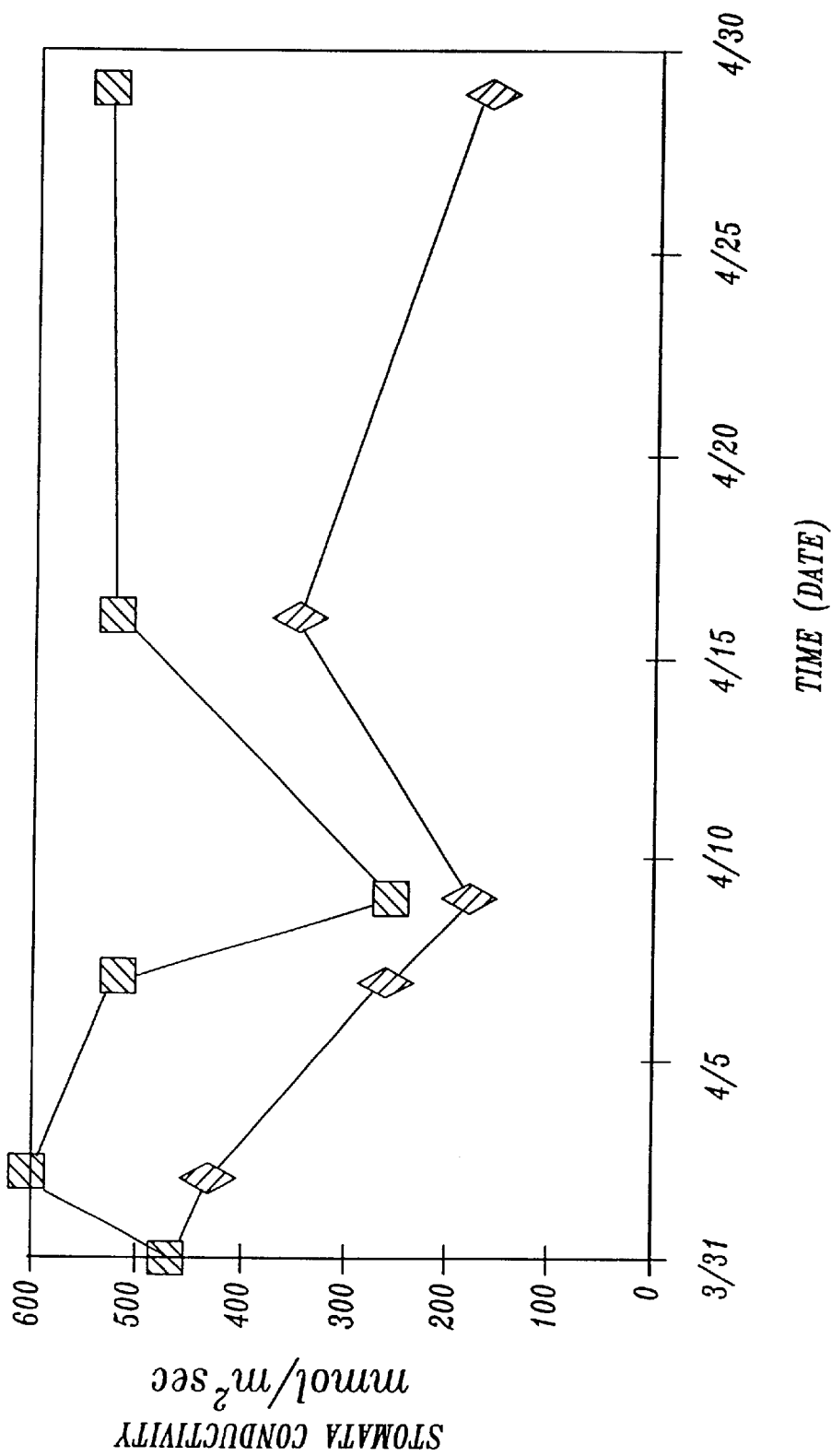
FIG. 3 is a graph of leaf stomata conductance over two months in control and chitosan-treated sunflower plants (values represent the mean of one experiment with seven plants per treatment)

Referring to FIG. 3, foliar application of chitosan on sunflower plants induced a decrease in stomata conductance in every treated plant during the growing period. The difference in stomata conductance between treated and control plants was more pronounced in the later part of the growing period (after April 20). The drop in stomata conductance in both treated and control plants on April 9 was likely due to changes in environmental conditions.

Figure 4:
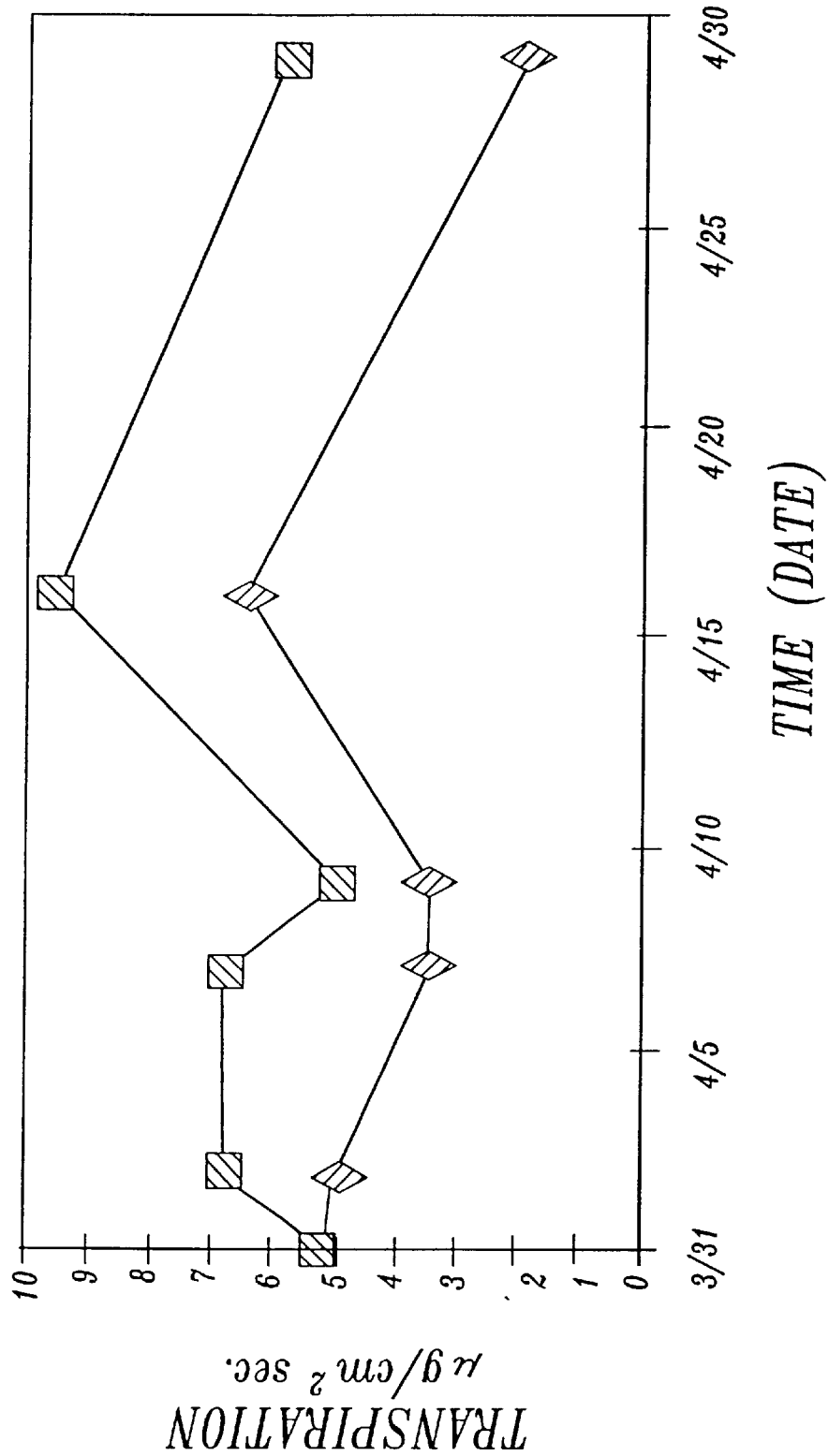
FIG. 4 is a graph of transpiration over two months in control and chitosan-treated sunflower plants (values represent the mean of one experiment with seven plants per treatment)

As shown in FIG. 4, foliar application of chitosan also resulted in reduced transpiration compared to control treated plants. The observed decrease in transpiration can be explained by a reduction in stomata conductance (closure of stomata to reduce water loss).

Example 2

Transpiration Reduction in Pepper Plants Grown in the Growth Chamber

The plant species used in this example were pepper (Capsicum sp.). Potted plants were grown in a temperature-controlled growth-chamber under metal halide lamps with a 13 hour light period. Average temperature in the growth chamber was 20° C., and relative humidity was 61%. Pots contained a greenhouse mix peat soil enriched with slow release fertilizer. Environmental conditions (light, temperature, and relative humidity) inside the growth chamber were monitored every 30 minutes during the experiment using standard environmental sensors such as a pyranometer, thermocouple psychrometer, relative humidity sensor and a datalogger. A set of 24 pepper plants were used to evaluate chitosan on drought resistance and transpiration. Two groups of 6 plants per group were watered to keep the water content near field capacity (optimally watered groups). Each of the 6 plants in one of these optimally watered groups received chitosan application as described below. The other 6 plants in the optimally watered group received the control carrier solution alone. Two other two groups of 6 plants per group were only watered when the soil reached the permanent wilting water potential (which corresponded to two to three days without watering). These two groups were designated water stressed. Each of the 6 plants in one of the water stressed groups received chitosan application as described below. The other 6 plants in the water stressed group received the control carrier solution alone.

Chitosan was sprayed onto the top surface and bottom surface of leaves as described in Example 1 using a simple hand sprayer. The control group received the carrier (lactate) alone at 0.1% (w/w) D/L-lactic acid pH adjusted to 4 and sprayed onto the leaves in the same fashion as the treated group. Both the treated group and the control group were sprayed once a week.

Daily transpiration rates were monitored by weighing the pots each day to record the corresponding water use and then refilling the water to field capacity.

Figure 5:
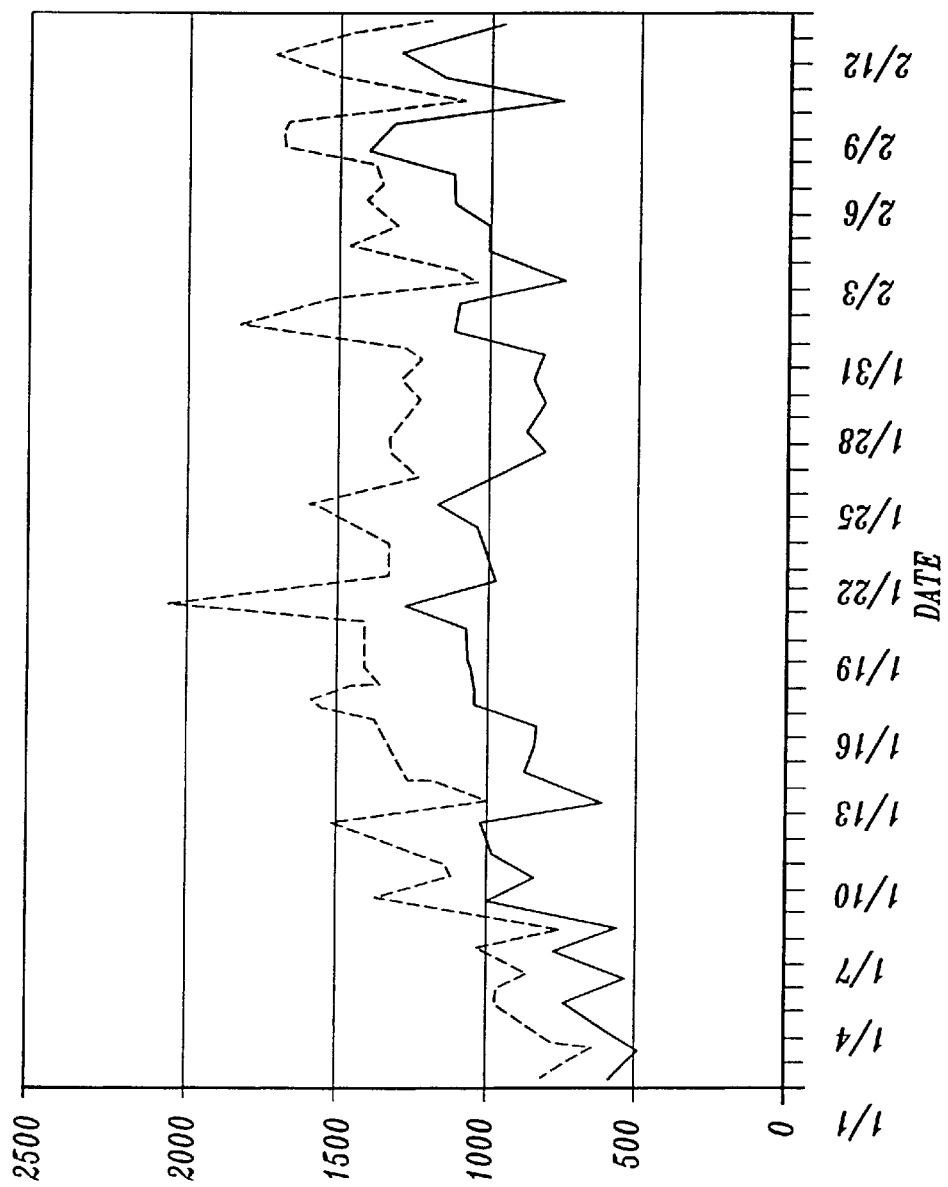
FIG. 5 is a graph of daily water use for control and chitosan-treated pepper plants.
Figure 6:
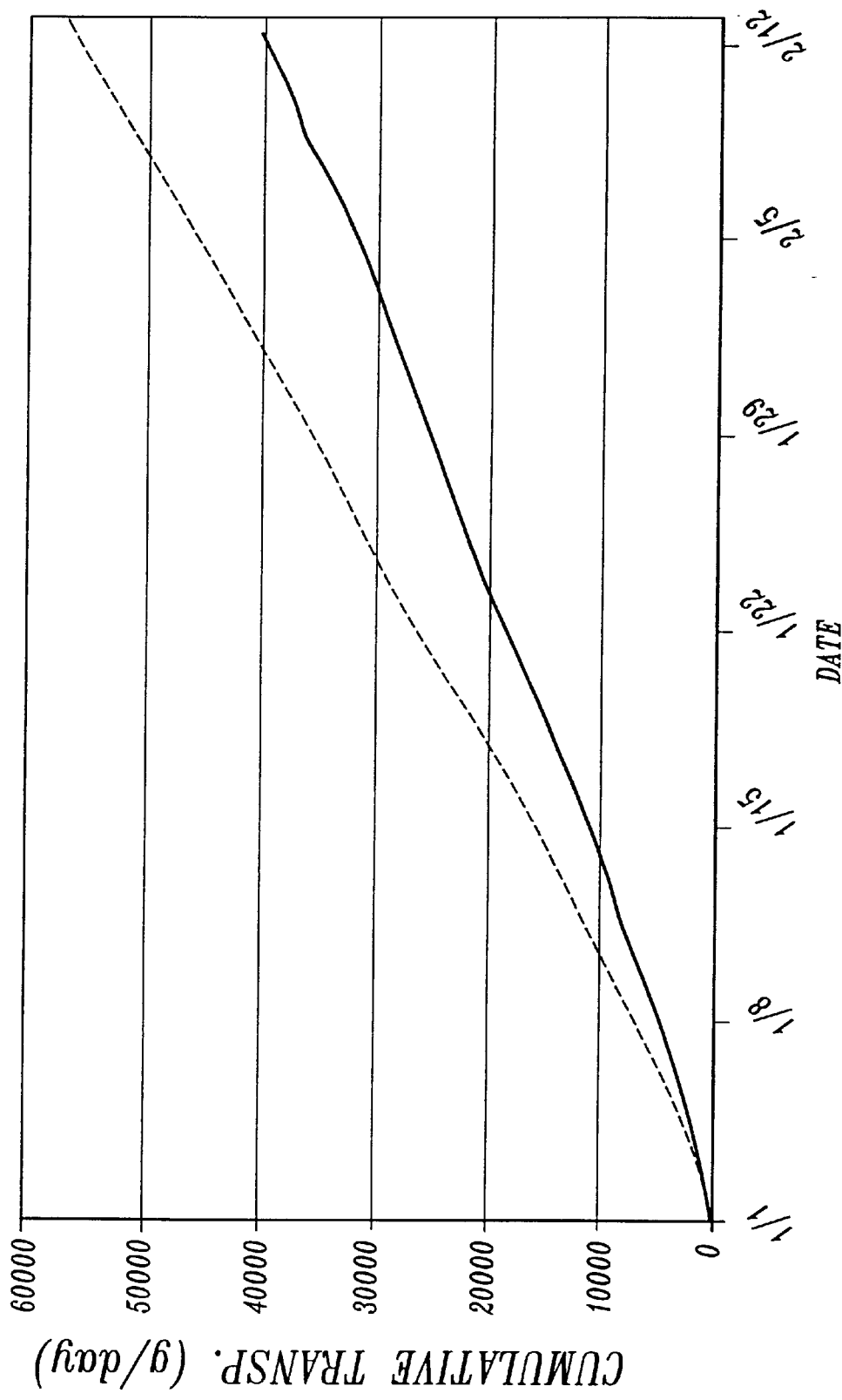
FIG. 6 is a graph of daily cumulative water use for control and chitosan-treated pepper plants.

As shown in FIG. 5, chitosan-treated plants that were optimally watered, exhibited a significant reduction in transpiration compared to control plants. The daily cumulative water use shown in FIG. 6 further demonstrates an overall reduction in transpiration in chitosan-treated plants compared to controls.

Figure 7:
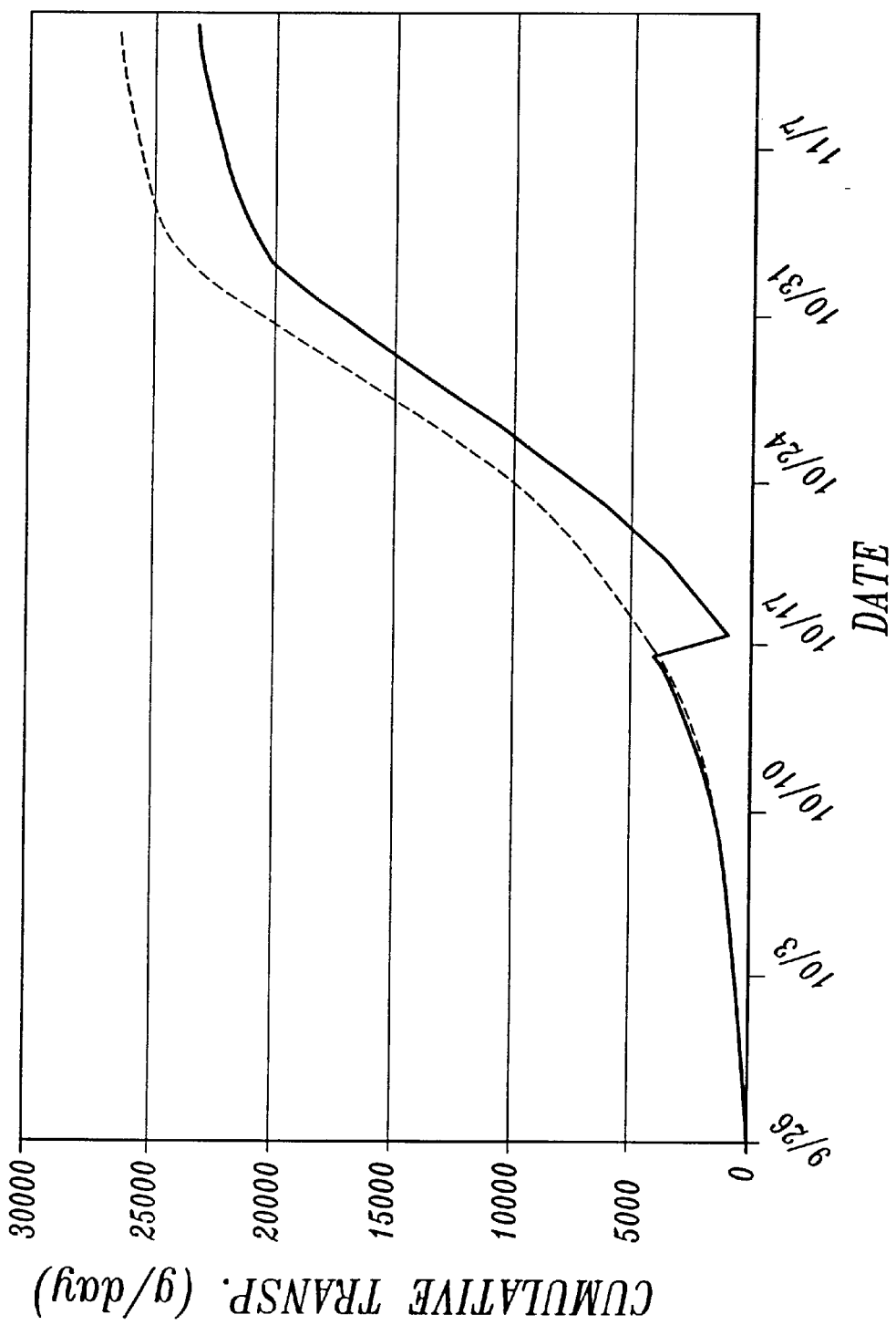
FIG. 7 is a graph of water use measured as cumulative transpiration in units of g/day under water-stressed conditions for control and chitosan-treated pepper plants.

Under water stressed conditions, the cumulative water use in control plants was consistently higher than that in chitosan treated plants as shown in FIG. 7. The reduced use of water by chitosan-treated plants under water stress (drought) conditions is most likely a direct result of reduced stomata conductance induced by chitosan.

Example 3

Reduced Water Use Under Field Conditions

Under both greenhouse and controlled growth chamber experiments, chitosan demonstrated a significant effect in reducing stomata conductance and transpiration. The results were consistent and statistically significant. Since the studies were conducted under controlled conditions, the findings were validated and verified under field conditions.

Corn (*Zea Maize*), pepper (Capsicum spp) and potato (*Solanum tuberosum*) were chosen for field studies. The experiment was performed in Pullman, Wash. (USA). An experimental plot was setup with 8 repetitions for every plant, in order to obtain statistically independent results. Eight rows were set up for every crop resulting in 24 separate rows. The treatment and control plots were set up following a randomized scheme. The plots were tilled to a depth of approximately 30 cm and a chemical fertilizer (16% N, 16% P, 16% K) was applied by incorporation into the soil during tillage.

Water Use Measurements. To measure water use of the plants, a dripping irrigation system was designed and constructed such that water was supplied to the plots when a threshold value of soil water content was reached. This allowed the measurement of water used in every single plot such that evaluation of water use differences between the control and chitosan treated crops could be monitored. The system was installed in such a way that every plant received a given amount of water determined by using constant rate water applicators. The applicators applied water at a constant rate 2 gal/hr (7.56 liters/hour). Irrigation pipes were activated by electrical valves. Soil water content (SWC) was measured continuously, using a Time Domain Reflectometer sensor installed in each of the twenty-four rows. Twenty-four transmission line oscillator (TLO) probes (model CS615-L water content reflectometer, Campbell Scientific Inc. Logan, Utah) were installed in the field. The sensors were monitored by a datalogger (model 23X, Campbell Scientific Inc., Logan, Utah). The probes were 30 cm long, and were buried vertically, such that average volumetric water content of the top 30 cm of the soil was measured. The probes were installed in the middle of the plant rows. The soil water content was measured every 60 seconds. Averages of the reading were output every 60 minutes and stored in the datalogger. The TLO were previously calibrated against gravimetric water contents and latter were converted to volumetric water content by using the bulk density. At the end of the day (midnight), SWC was measured. If, for every specified row, SWC was below 25% in volume, the irrigation system was activated and it irrigated for the total time required to replenish the specified soil volume to Field Capacity (FC). Every plant was irrigated by one drip irrigator, having a steady irrigation rate of 2 gal/hr. The total amount of water applied per row was obtained by multiplying the minutes of irrigation per day by the irrigation rate by the number of drip irrigators, while the total amount of water per plant was obtained by considering only one drip irrigator. The application rate was set in such a way that the irrigation rate was always less than the infiltration rate in order to avoid the formation of ponds or the occurrence of runoff. The datalogger (controlling the irrigation system) was programmed in the following way: the water contents were read by the TLO probes, the data for every row were compared to the threshold value of 0.25 $m^3/m^3$ (Field Capacity). If the values were below FC, the irrigation started and ran until the soil water content was replenished to FC. In this way, the soil was kept at a constant water content approximately corresponding to FC. FC value was calculated by using an empirical equation that calculates it by knowledge of soil textural data. Two parameters obtained from soil textural data are slope of the water retention curve and air entry potential. The equations used were those as described in *Soil Physics With Basic* by Gaylon S. Campbell, published by Elsevier Science Publishing (1985). Values of the above parameters are used to obtain values of soil water content at the corresponding soil water potential of −33J/Kg (defined Field Capacity). Soil particle size analysis was performed in order to obtain the mentioned parameters.

Weather Data. Weather data were collected including daily rainfall, daily average air temperature, daily global solar radiation and daily average wind speed. Hourly rainfall was summed to obtain the cumulative value over a day, air temperature was averaged and max and min temperature were recorded, global solar radiation was summed to obtain cumulative daily data, wind speed was averaged, relative humidity was used together with air temperature to calculate the vapor pressure deficit that was then averaged. Weather data show that the experimental plot was setup in a site with a low cumulative rainfall (116.38 mm over the period 168 to 307 days of the year).

Chitosan application. The chitosan concentration used was 0.1% (w/w) in 0.1% D/L-lactic acid applied uniformly as a foliar spray for each crop. The control plants were treated in the same way using the carrier alone (0.1% D/L-lactic acid). Foliar treatments were applied once per week. A total of 1500 ml of the chitosan solution was applied over a total of 62 corn plants at one application per week; 1500 ml over a total of 20 pepper plants at one application per week; and 1500 ml over a total of 40 potato plants at one application per week.

Biomass Determination. Total Dry Biomass (TDB) was measured for the entire plant and for different sections (such as stems, leaves and yield) at the end of the growing season for Corn and Pepper. Dry weight determinations were made after drying plants at 60° C. for three days.

Tubers only were measured for Potato. Specific gravity, USDA class, number and quality were recorded for Potato tubers according to the standards suggested by the USDA. Standards published by the USDA (48 FR 10801) were followed to provide a classification of tubers in Class 1 and Class 2.

Figure 8:
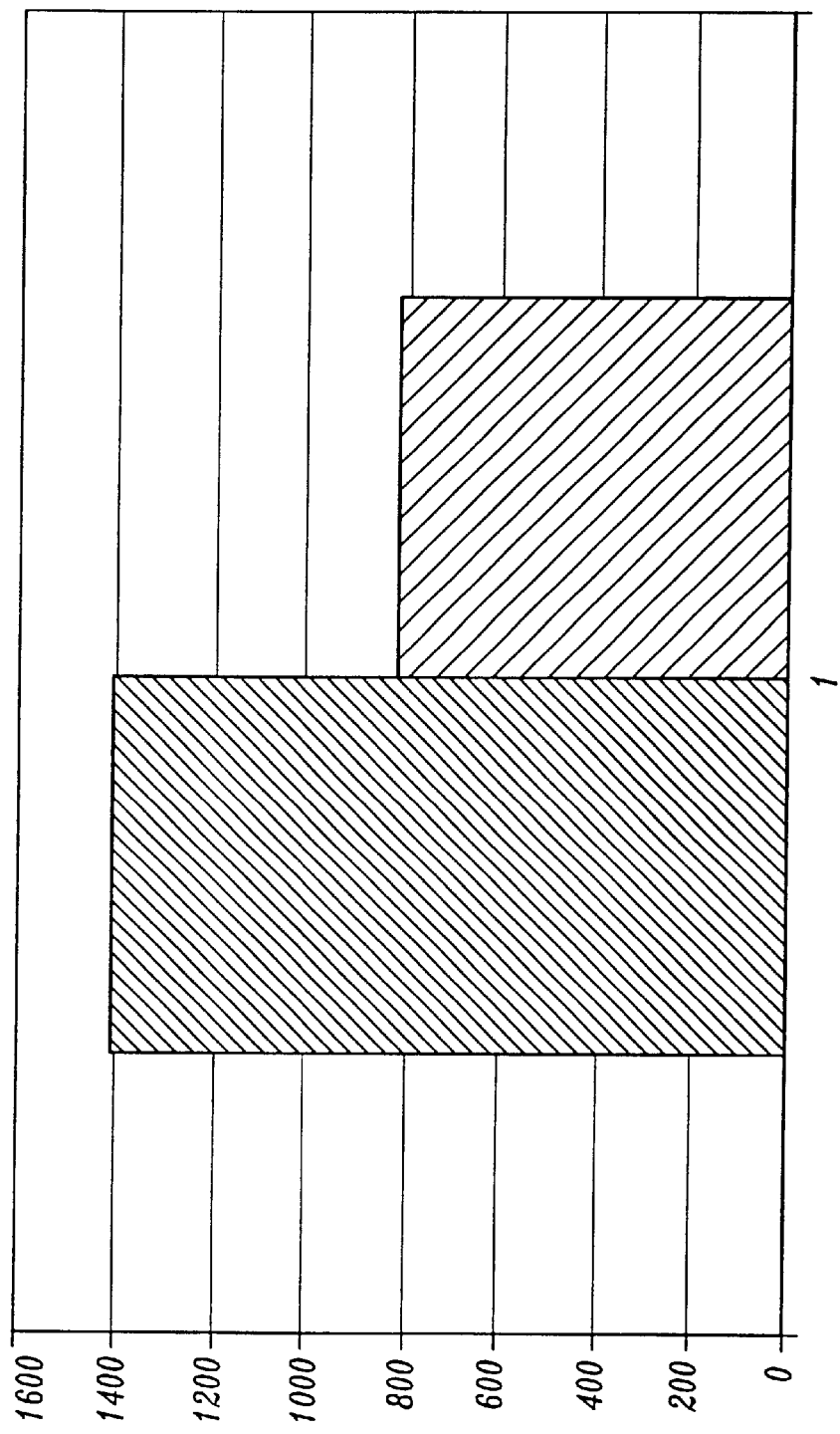
FIG. 8 is a graph of cumulative water use (repetitions summed) for control (C) and chitosan-treated (T) pepper plants.
Figure 9:
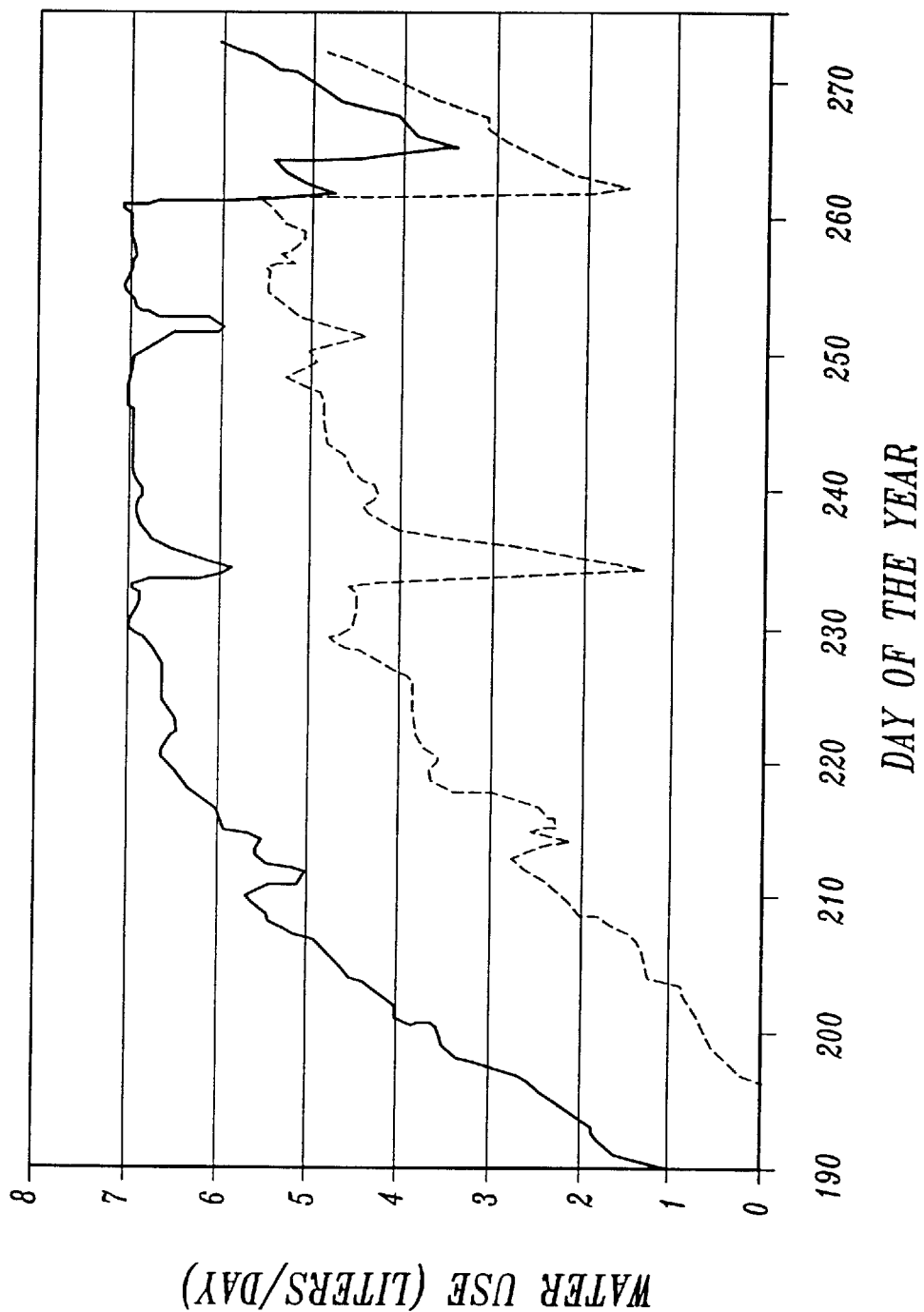
FIG. 9 is a graph of daily average water use (liters/day) for control and chitosan-treated pepper plants.
Figure 10:
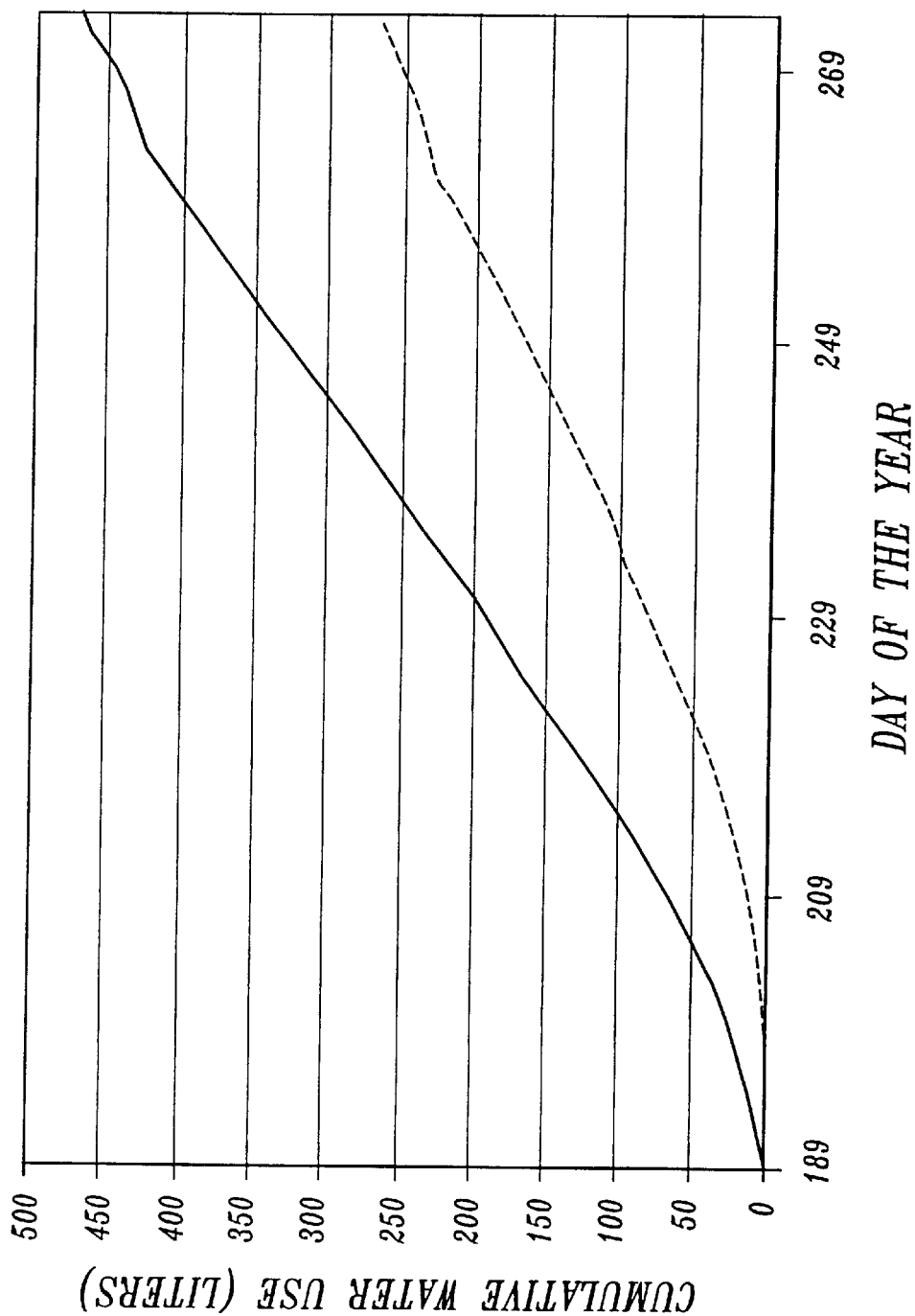
FIG. 10 is a graph of daily average cumulative water use for control and chitosan-treated pepper plants.

As shown in FIG. 8, the total water used by pepper plants in the control group was 1406 liters and the total for chitosan treated was 805 liters. Paired comparison and Single factor Analysis of Variance (ANOVA) were conducted between chitosan treated and control plants at a significance level of 95%. The difference between the chitosan treated and control treated plants is statistically significant and the treated plants showed a 57.5% smaller cumulative water use compared to controls. The daily average water use comparison is shown in FIG. 9. The depressions in water use correspond to days at high rainfall, where the irrigation system stopped applying water because the rainfall water replenished the soil. As illustrated in FIG. 10, the daily average cumulative water use by peppers was significantly less in chitosan-treated plants compared to controls.

Figure 11:
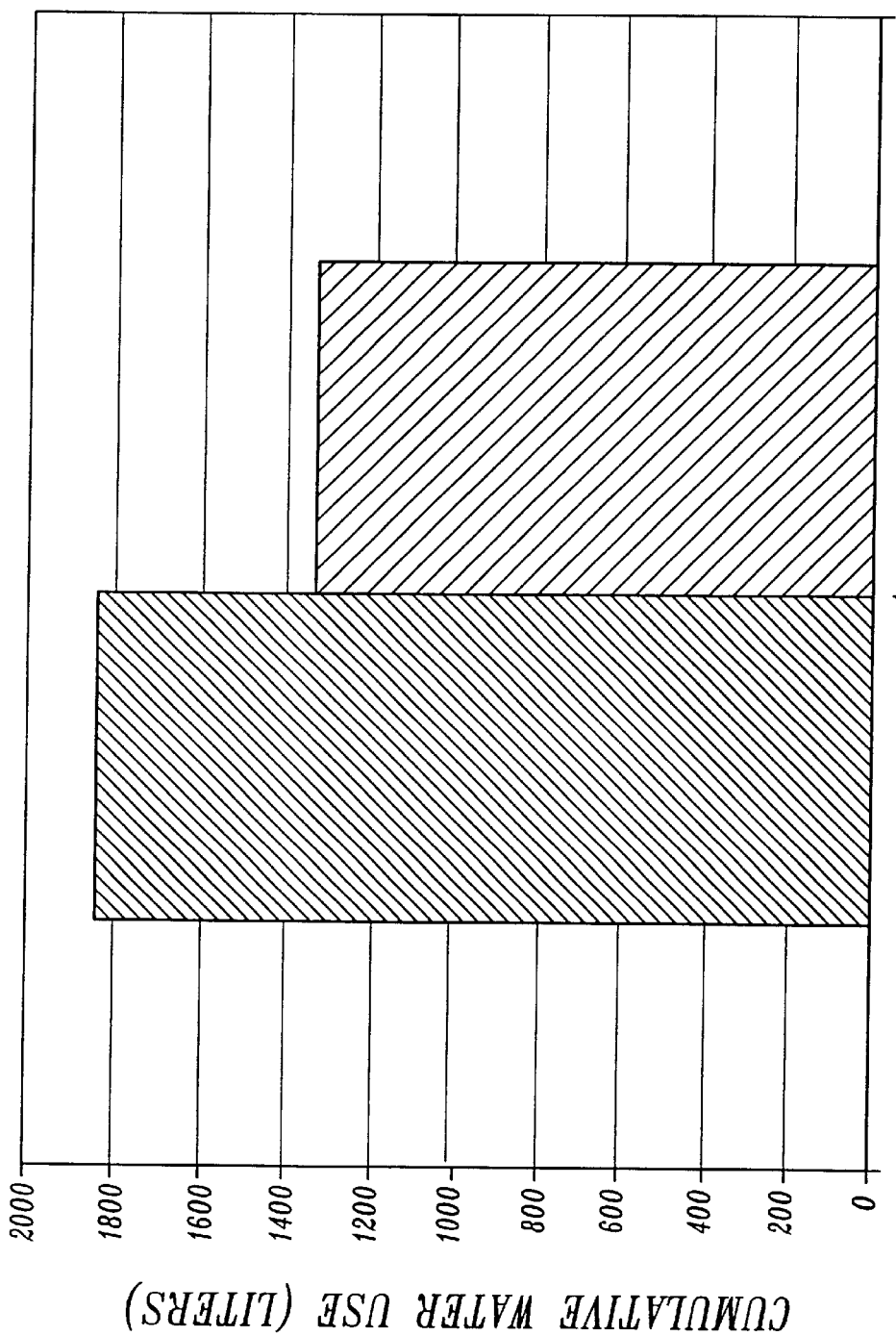
FIG. 11 is a graph of cumulative water use for control and chitosan-treated corn plants.

The effect of chitosan application on water use in corn was significant at a 90% level of confidence, resulting in a decreased water use of 28.7% compared to non-treated plants. The cumulative water use for the eight rows (four treatment and four controls) has been summed and plotted as shown in FIG. 11.

Biomass Production and Water Use Efficiency in Peppers. Total fresh matter (TFM) or peppers were harvested during the growing season, while the leaves and stems (TDM) have been harvested at the end of the growing season. A single factor Analysis of Variance failed to show any statistically significant differences in TFM production between chitosan treatment and controls. Total dry matter (TDM) was determined for chitosan treated and non-treated plants and the dry weight ratio of leaves to stems (L/T) was determined. The L/T ratio for control plants was equal to 1.4 which was statistically significant from the L/T ratio of chitosan treated plants which was 1.7. This finding indicates that chitosan treatment switched the partition coefficient toward the production of leaves. In light of these results, the Water Use Efficiency was determined. Water Use Efficiency (WUE) is defined as the ratio between the total yield and the total plant water use (TWU), WUE= TDM/TWU. This index gives an important indication on the ability of the crop to utilize water to produce yield. Table 1 shows the WUE values for three replicates of chitosan treated and three replicates of control plants. As shown in Table 1, the Water Use Efficiency (WUE) for chitosan treatment is much higher compared to the control treated and their Water Use Efficiency Ratio (WUE treated/WUE control) is equal to 1.67. Since there was no statistically significant difference in biomass production between chitosan treated and controls, it can be concluded, that pepper plants treated with chitosan, produce the same amount of biomass as non-treated controls by using 57% less water.

TABLE 1

Yield, water use, and water use efficiency for pepper.

| Description | Yield (g) | Water Use (liters) | Water Use Efficiency (%) |
|---|---|---|---|
| Control | 3314 | 533.65 | 6.21 |
| 12C | 3558 | 506.82 | 7.02 |
| 13C | 2641 | 365.59 | 7.22 |
| SUM | 9513 | 1406 | 6.77 |
| Treated | 2940 | 282.55 | 10.40 |
| 11T | 2993 | 326.92 | 9.15 |
| 14T | 3178 | 195.85 | 16.22 |
| SUM | 9111 | 805 | 11.31 |

Figure 12:
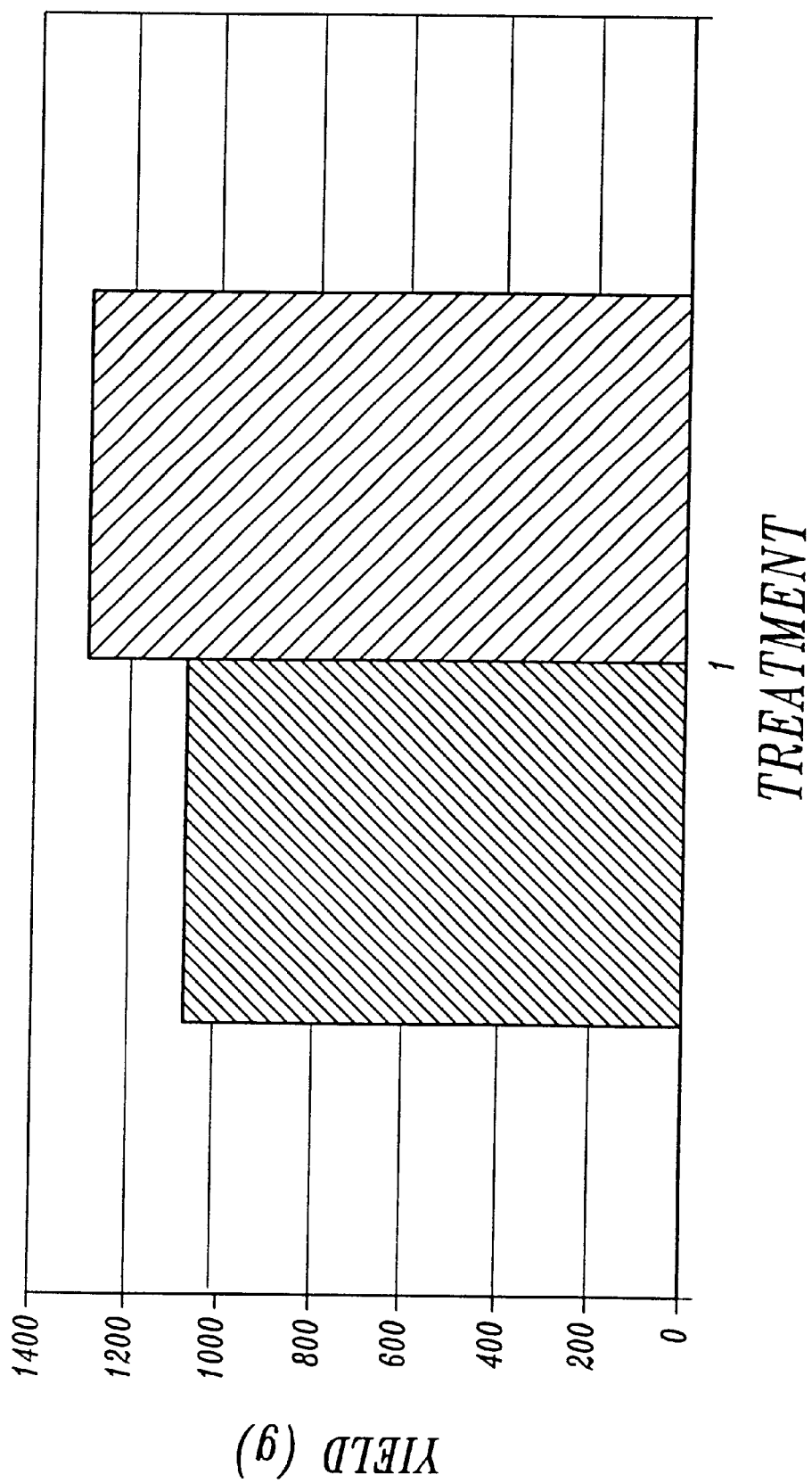
FIG. 12 is a graph of cumulative yield for control and chitosan-treated corn plants.
Figure 13:
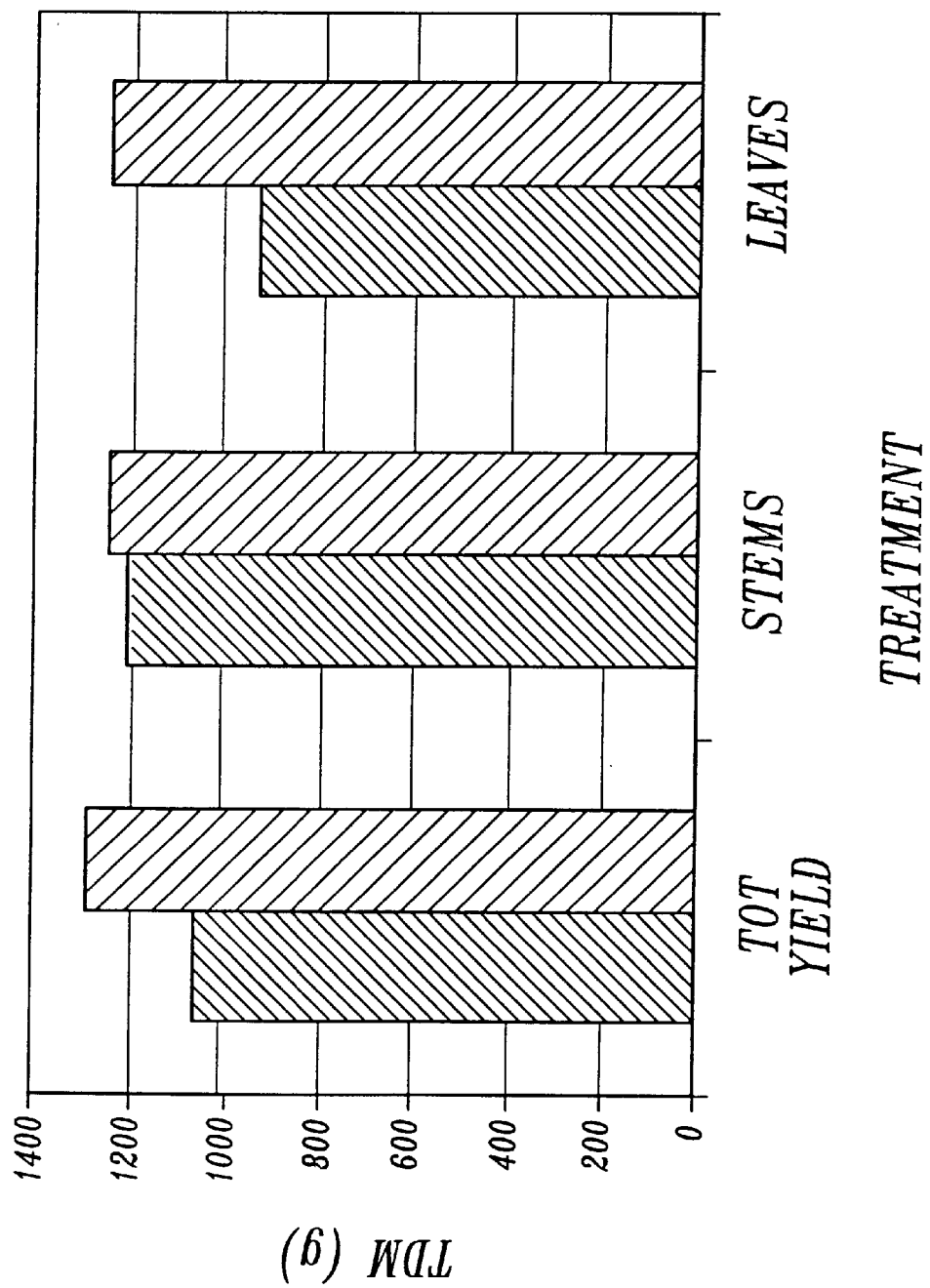
FIG. 13 is a graph of corn production components average cumulative water use for control and chitosan-treated corn plants.

Biomass Production in Corn. The total dry matter (TDM) was determined for chitosan-treated and control plants. FIG. 12 shows the cumulative yield production of dry matter (corn). A single factor Analysis of Variance shows statistically significant differences at the 95% level of confidence between treated and control. The treated plants showed a higher biomass production compared to non-treated controls. The relative difference was 20.6%. The partition between leaves, stems and yield for corn was investigated as shown in FIG. 13. Relative differences for the partition are 24.6% for leaves, 3.4% for stems and 17.3% for yield. These results show that biomass production was higher for treated plants for all three components analyzed. The L/T ratios were also examined. The control plants exhibited an L/T ratio of 0.7 compared to 1.04 for chitosan treated. These results indicate, as was observed in peppers, that chitosan application induced a different partitioning in corn resulting in higher production of leaf tissue relative to stem tissue.

Figure 14:
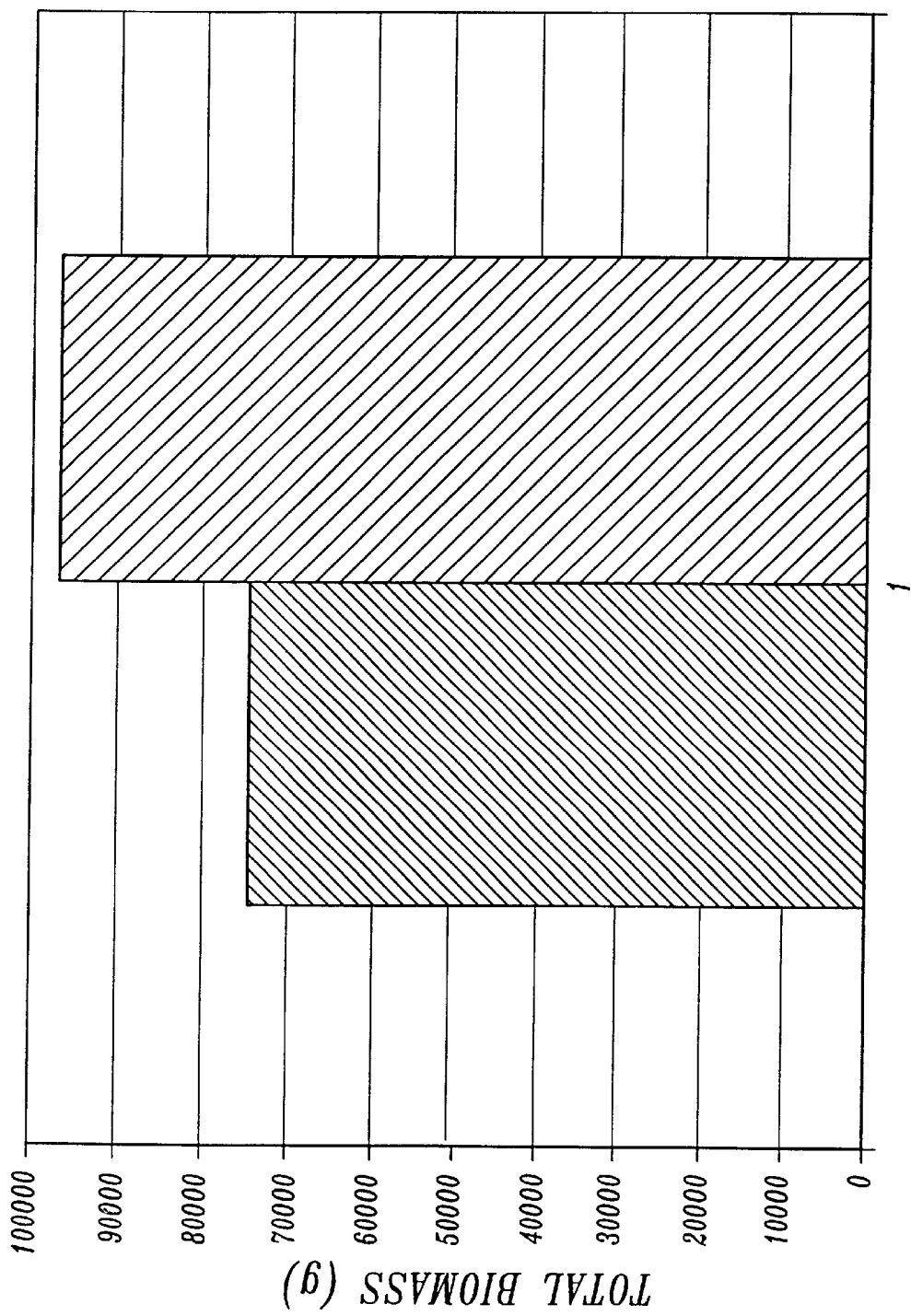
FIG. 14 is a graph of cumulative yield for control and chitosan-treated potato plants.

Biomass Production in Potato. Biomass determinations for potato were conducted on tubers only. Quantitative determinations by weight were determined for chitosan treated and controls. As shown in FIG. 14, the chitosan treated plants displayed a higher biomass production with statistically significant differences at the 95% level of confidence. The total tuber production for treated plants was 96,113 g compared to control plants of 74,719 g. The average yield was 24,028 g for treated plants and 18,680 g for control plants. The biomass production was 23% higher for treated plants compared to controls.

Qualitative Differences in Potato Tuber Biomass. In order to investigate qualitative differences in potato tuber production, the ratio of Class 1/ total number of tubers was calculated. As shown in Table 2, the ratio was 181/1090= 0.16 for chitosan treated and 107/830=0.12 for controls. This result indicates that chitosan treated plants produced a higher number of tubers belonging to Class 1, demonstrating that chitosan treatment increases the production of higher quality tubers. This result may be indicative of a partitioning effect as a result of increased Water Use Efficiency.

TABLE 2

Number of tubers belonging to Class 1 and Class 2.

| Description | Class 1 (number) | Class 2 (number) |
|---|---|---|
| Chitosan treated row 24 | 66 | 236 |
| Chitosan treated row 18 | 23 | 277 |
| Chitosan treated row 19 | 35 | 250 |
| Chitosan treated row 21 | 57 | 146 |
| Sum Total | 181 | 909 |

TABLE 2-continued

Number of tubers belonging to Class 1 and Class 2.

| Description | Class 1 (number) | Class 2 (number) |
|---|---|---|
| Control row 17 | 30 | 256 |
| Control row 20 | 19 | 216 |
| Control row 22 | 14 | 214 |
| Control row 23 | 44 | 144 |
| Sum Total | 107 | 830 |

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for reducing plant transpiration, comprising:

applying a chitosan composition to a watered plant wherein the chitosan composition is an aqueous solution comprising chitosan and a nonphytotoxic acid and wherein the chitosan composition is applied to the plant's foliage in an effective amount to reduce stomatal conductivity.

2. The method of claim 1 wherein the chitosan is derived from fungal mycelia.

3. The method of claim 1 wherein the composition is applied to a plant's foliage once per week.

4. The method of claim 1 wherein the chitosan composition is also applied to the plant's root system.

5. The method of claim 1 wherein the chitosan is present in the composition in an amount from about 0.05% to about 10% by weight based on the total weight of the composition.

6. The method of claim 1 wherein the nonphytotoxic acid is present in the composition in an amount from about 0.05% to about 10% by weight based on the total weight of the composition.

7. The method of claim 1 wherein the nonphytotoxic acid is selected from the group consisting of lactic, pyruvic, succinic, fumaric, glutamic, aspartic, malic, maleic, and sorbic acids, and mixtures thereof.

8. The method of claim 1 wherein the nonphytotoxic acid comprises lactic acid.

9. A method for reducing transpiration, comprising:

applying a chitosan solution to a watered plant wherein the chitosan composition is an aqueous solution comprising chitosan and a nonphytotoxic acid and wherein the chitosan composition is applied to the plant's roots in an effective amount to reduce stomatal conductivity.

10. A composition comprising an aqueous solution of chitosan, a nonphytotoxic acid, and an antitranspirant selected from the group consisting of sorbitol and mannitol, wherein the chitosan has a molecular weight in the range from about 10,000 to about 50,000 Daltons.

11. The composition of claim 10 wherein the chitosan is present in the composition in an amount from about 0.05% to about 10% by weight based on the total weight of the composition.

12. The composition of claim 10 wherein the nonphytotoxic acid is present in the composition in an amount from about 0.05% to about 10.0% by weight based on the total weight of the composition.

13. The composition of claim 10 wherein the nonphytotoxic acid is selected from the group consisting of lactic, pyruvic, succinic, fumaric, glutamic, aspartic, malic, maleic, and sorbic acids, and mixtures thereof.

14. The composition of claim 10 wherein the nonphytotoxic acid comprises lactic acid.

15. The composition of claim 10 wherein the chitosan is derived from fungal mycelia.

16. The composition of claim 10, wherein the antitranspirant is sorbitol.

17. The composition of claim 10, wherein the antitranspirant is mannitol.

18. A composition comprising an aqueous solution of chitosan, lactic acid, and an antitranspirant selected from the group consisting of sorbitol and mannitol, wherein the chitosan has a molecular weight in the range from about 10,000 to about 50,000 Daltons, wherein chitosan is present in about 0.1% by weight based on the total weight of the solution, and wherein the lactic acid is present in about 0.1% by weight based on the total weight of the solution.

* * * * *